(12) United States Patent
Bodewadt

(10) Patent No.: US 10,111,671 B2
(45) Date of Patent: Oct. 30, 2018

(54) IMPLANT DELIVERY SYSTEM

(71) Applicant: COOK MEDICAL TECHNOLOGIES LLC, Bloomington, IN (US)

(72) Inventor: Tue Thuren Bodewadt, Solroed Strand (DK)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 1167 days.

(21) Appl. No.: 13/802,963

(22) Filed: Mar. 14, 2013

(65) Prior Publication Data

US 2013/0296915 A1    Nov. 7, 2013

(30) Foreign Application Priority Data

May 2, 2012 (GB) .................... 1207619.6

(51) Int. Cl.
  *A61B 17/12* (2006.01)
  *A61F 2/966* (2013.01)
  *A61B 17/00* (2006.01)
  *A61B 50/30* (2016.01)

(52) U.S. Cl.
  CPC .... *A61B 17/1214* (2013.01); *A61B 17/12031* (2013.01); *A61B 17/12113* (2013.01); *A61F 2/966* (2013.01); *A61B 50/30* (2016.02); *A61B 2017/0053* (2013.01); *A61B 2017/12095* (2013.01); *A61F 2002/9665* (2013.01)

(58) Field of Classification Search
  CPC .... A61B 2017/12095; A61B 17/12031; A61B 17/12036; A61B 17/12113; A61B 17/1214
  See application file for complete search history.

(56) References Cited

U.S. PATENT DOCUMENTS

| | | | | |
|---|---|---|---|---|
| 5,234,437 A | * | 8/1993 | Sepetka | A61B 17/12022 600/585 |
| 5,258,000 A | * | 11/1993 | Gianturco | A61B 17/0057 606/151 |
| 5,312,415 A | * | 5/1994 | Palermo | A61B 17/12022 606/108 |
| 5,984,929 A | | 11/1999 | Bashiri et al. | |
| 6,190,373 B1 | | 2/2001 | Palermo et al. | |
| 2006/0025803 A1 | * | 2/2006 | Mitelberg | A61B 17/12022 606/200 |

(Continued)

FOREIGN PATENT DOCUMENTS

DE    93 20 839.1    4/1995
DE    102007038446 A1    8/2007

(Continued)

*Primary Examiner* — Kathleen Holwerda
*Assistant Examiner* — Sarah Simpson
(74) *Attorney, Agent, or Firm* — Brinks Gilson & Lione

(57) ABSTRACT

A delivery system (50) for a detachable medical device (10) comprises a first helical wire (12) attached to the medical device, a second helical wire (18) attached to a deployment member (16) and a wire coil (30) which is arranged to interconnect the helical wires (12, 18). A pull on a release wire (32) at one end of the coil (30) detaches the coil from at least one of the helical wires whereby to detach the medical device (10) from the deployment member (16). In a modification a release coil (130) is arranged between concentric helical wires (112, 118).

13 Claims, 3 Drawing Sheets

(56) References Cited

U.S. PATENT DOCUMENTS

2008/0103585 A1    5/2008  Monstadt et al.
2010/0268201 A1*  10/2010  Tieu ................ A61B 17/12022
                                                               606/1
2011/0295303 A1   12/2011  Freudenthal

FOREIGN PATENT DOCUMENTS

EP          0 717 969 A2    6/1996
EP          0 717 969 A3   11/1996
WO     WO 2010/092174 A2    8/2010

* cited by examiner

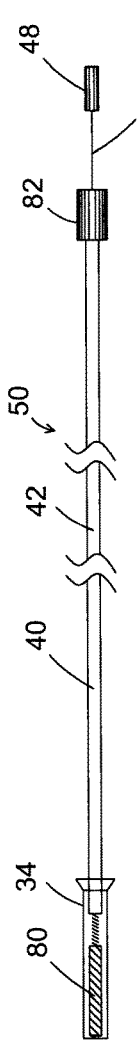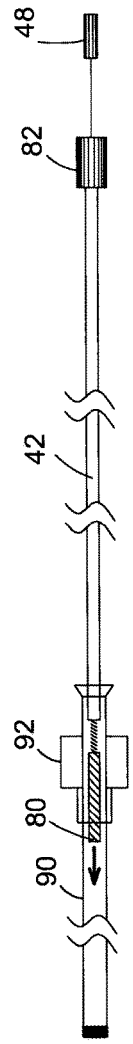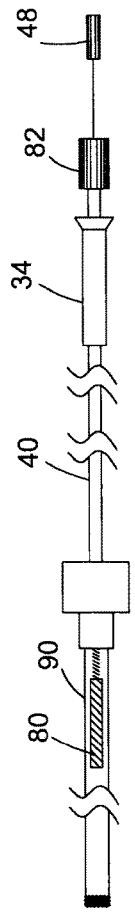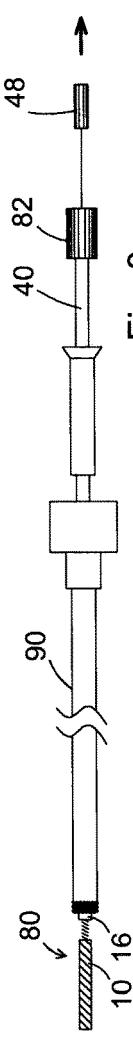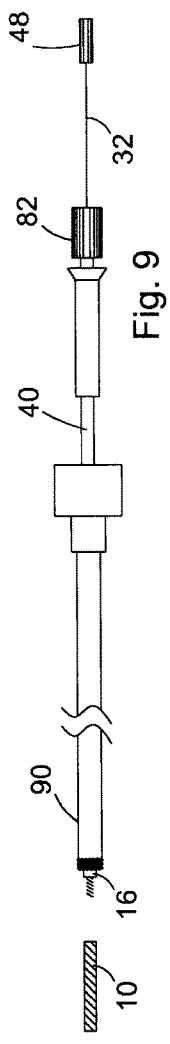

IMPLANT DELIVERY SYSTEM

CROSS-REFERENCE TO RELATED APPLICATIONS

This application is related to and claims the benefit of priority to GB 1207619.6, filed on May 2, 2012 which is incorporated herein by reference in its entirety.

TECHNICAL FIELD

The present invention relates to an implant delivery system and in particular to a system for releasing implantable devices, such as coils, into blood vessels and body cavities such as aneurysms.

BACKGROUND ART

Various systems are known for releasing a coil after it has been advanced by an introducer system through the vasculature of a patient. For example, in US 2010/0268201 the implantable device is fixed to its delivery system by means of a looped tether. US 2008/0103585 discloses an example of a system in which a coil is released electrolytically.

In other systems, such as the Jackson system, coils are connected to a delivery wire by a wound junction. This screw connection is detached by rotating the wire by means of a handle. This can be inconvenient in that it requires the handle to be rotated many times.

Aspects of the present invention seek to provide an improved delivery system which permits a simple and rapid method of release.

Other aspects of the present invention seek to provide an improved delivery system permitting release of implants successively.

According to a first aspect of the present invention, there is provided a delivery system for a detachable medical device, the system comprising a first release portion on the medical device, a second release portion on a deployment member and a releasing element which is arranged to interconnect the first and second release portions, the first and second release portions each having an element defining a respective path of wound configuration and the releasing element comprising a wire coil which engages both of the wound paths to hold the release portions together, the wire coil having a pull release wire attached to one end thereof, the releasing element being detachable from at least one of the release portions by a pull on said release wire, whereby to detach the release portions from each other.

In one preferred embodiment, the release portions are substantially in alignment and each release portion comprises a respective helically wound wire with turns forming a hollow core, the wire coil of the releasing element having turns which engage with end turns of the wires of both the release portions.

As used herein, the term "wire" designates any suitable elongate element of metal, plastics or any other suitable material; it may have any suitable size and shape and may have a cross-section which is constant or which varies along its length and may be circular or non-circular, such as elliptical, square, rounded off square or polygonal.

The ends of the helically wound wires of the release portions may be in a substantially mutually abutting relationship.

In a modification the release portions are concentrically arranged helically wound wires, the wire coil of the releasing element having turns, the exterior side of which engage with the interior of turns of the outer wire and the interior side of which engage with the exterior of turns of the inner wire.

The wire forming the coil may have an elongate cross-section.

In preferred embodiments, the second release portion comprises a tubular part at the end of its wire remote from the first release portion, and the release wire extends through the tubular part.

The material of the wire of the releasing element is substantially softer than the material of the helical wires of the release portions.

In another modification the release portions are substantially in alignment and wherein each release portion comprises an externally threaded member, the wire coil of the releasing element having turns which engage with the external threads of both release portions. In this case, the release portions preferably have a uniform circular cross-section.

The wire coil may be of resilient material.

According to a second aspect of the present invention, there is provided an introducer system for an implantable medical device comprising an introducer device, a pusher member connected to the introducer device, and a handle movable relative to both the introducer device and the pusher member, a deployment member located distally of said pusher member and a medical device located distally of said deployment member, the medical device having a first release portion, the deployment member having a second release portion, and a releasing element which is arranged to interconnect the first and second release portions, the first and second release portions each having an element defining a respective path of wound configuration and the releasing element comprising a wire coil which engages both of the wound paths to hold the release portions together, the releasing element being connected to said handle via a release wire, the arrangement being such that, upon a proximal movement of the handle relative to the rest of the introducer device, the releasing element is detachable from at least one of the release portions whereby to detach the release portions from each other.

In preferred embodiments, the pusher member has an interior lumen and the release wire passes from the wire coil to the handle through said lumen.

The release wire is preferably integral with the wire coil.

BRIEF DESCRIPTION OF THE DRAWINGS

Preferred embodiments of the present invention will now be described, by way of example only, with reference to the accompanying drawings, of which:

FIG. 5 shows a delivery system for the assembly of FIG. 4;

FIG. 6 shows the introduction of the delivery system of FIG. 5 into a delivery catheter;

FIGS. 7 to 9 show further steps in the deployment of the assembly;

Referring to the drawings, FIG. 1 shows an implantable medical device 10 in the form of an embolization coil. The proximal end of the coil is formed as a first release portion in the form of a helically wound wire 12. As used herein the term "proximal" designates the end of a component which is nearer to an operator in use, e.g. a physician controlling the deployment apparatus. The term "distal" means designates the end of a component which is further away from an operator.

FIG. 2 shows the distal end of a deployment device or member 16 which is formed as a second release portion in the form of a helically wound wire 18. The windings formed by both wires 12 and 18 have hollow cores and they have substantially the same diameter and substantially the same pitch. Deployment device 16 is tubular and defines an interior lumen 14.

FIG. 3 shows a releasing element 30 for use with devices 10 and 16. Releasing element 30 comprises a helical wire coil 36, the windings of which have substantially the same diameter and pitch as the wires 12 and 18. A straight release wire portion 32 extends from the proximal end of wire coil 36.

FIG. 4 shows an implantable assembly 80 comprising the members 10, 16 and 30. It will be seen that the respective ends 27, 28 of the wires 12 and 18 are in a mutually facing relationship. The release wire portion 32 extends through the lumen 14 of device 16.

Coil 36 is of a resilient material such as nitinol or soft steel. To attach the wires 12, 18 to the coil 36, the wires can effectively be screwed in from opposite ends. The release members 10, 30, 16 are preferably manufactured and supplied in this pre-assembled form, in a sterile environment within sealed packaging.

Figure 1:
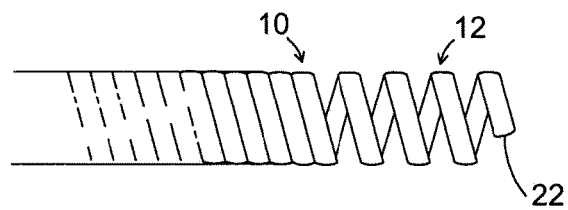
FIG. 1 is a side view of an implantable medical device of a first embodiment of the present invention.
Figure 2:
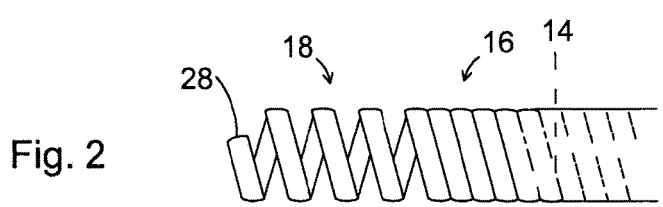
FIG. 2 is a side view of a deployment device of the first embodiment.
Figure 3:
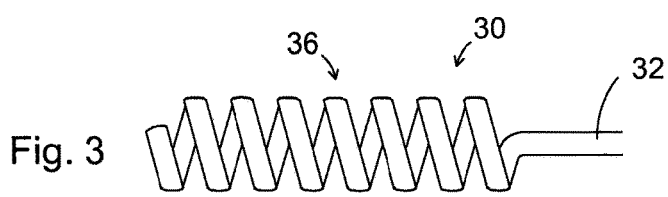
FIG. 3 is a side view of a releasing element of the first embodiment.
Figure 4:
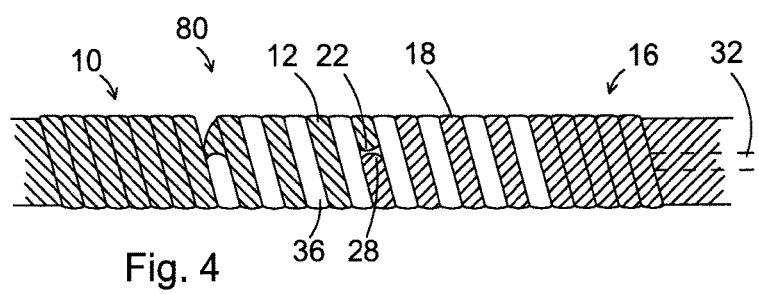
FIG. 4 is a side view showing an assembly comprising the members of FIGS. 1 to 3.

A delivery system 50 for the assembly of FIG. 4 is shown in FIG. 5. The wires 12, 18 and coil 36 are located within a rigid protection sleeve 34 which serves as the sealed packaging. A tubular member 40 in the form of a pusher tube enters the proximal end of sleeve 34 and has its distal end in contact with the proximal end of device 16. The pusher tube 40 defines an interior lumen 42 through which passes the release wire 32.

The distal end of pusher tube 40 is connected to a handle 44. Release wire 32 passes through a lumen in the handle to a knob 48 which can be pulled relative to handle 44 to pull the release wire 32.

To deploy the assembly 80, it is loaded with the distal end of the tubular member 40 into the proximal end of a delivery catheter 90, FIG. 6. A surrounding hub 92 is integral with the catheter at the proximal end thereof.

FIG. 7 shows the continued advance of the assembly 80 through the catheter. During this process, the sleeve 34 is relatively retracted towards the handle 82.

With the assembly 80 at the distal end of delivery catheter 90, and with the distal end of catheter 90 at the desired deployment site in the patient's vasculature, the medical device 10 is then advanced beyond the distal end of the sheath catheter 90 by retracting the sheath, or by pushing the deployment device 16 with pusher tube 40, or by a combination of both actions, see FIG. 8.

Until this point in the procedure, means (not shown) are provided for holding handle 82 and knob 48 in a relatively fixed relationship. When the medical device 10 has completely left the catheter 90 and is in its final position, knob 48 is then pulled. This pulls the release wire 32 which, due to the flexible nature of wire coil 36, pulls the proximal end of the coil slightly radially inwardly and then axially in the proximal direction. As pulling on knob 48 and wire 32 continues, the wire coil 36 completely unwinds from wire 18 and then from wire 12, see FIG. 9. At the end of the procedure, wire 32 can be completely retracted from the deployment system and medical device 10 is completely released from the deployment system.

Part or all of the deployment system 50 can then be removed and another set of releasing members can be loaded into the system for successive deployment.

An advantage of the above-described arrangement is that the medical device 10 and the deployment device 16 can be separated by a simple operation in a carefully controlled manner. Separation of the devices does not require a long unscrewing procedure. Furthermore, the withdrawal can be undertaken without sudden movements, which might displace the medical device in an undesired manner. Moreover, reloading of the release members is a simple operation, which is advantageous when a plurality of implants, such as embolization coils, need to be deployed in succession.

The interconnection of members 10, 16 and 30 to form assembly 80 employs unidirectional rotation throughout. This is a single process and avoids undesired distortion of the members.

The wire coil 30 is preferably of a material which is softer and more deformable than the material of the wires 12 and 18.

The wire coil is preferably of a resilient material.

Preferred materials for the wire coil are nitinol or soft steel.

The release wire 32 can be of the same material as wire coil 36 and can be integral therewith or fixedly attached thereto. Alternatively, wire 32 can be of a different material from coil 36.

The wires 12, 18 can be of the same material as their respective devices 10, 16 and can be integral therewith or fixedly attached thereto. Alternatively, one or both wires 12, 18 can be of a different material from their respective device.

Instead of a coil 10, the implantable device can be a stent, a stent graft, a filter, a valve or any other prosthesis. When the device is an embolization coil, it is advantageous if the wire 12 is made uniformly therewith, since after deployment it can adopt the role of contributing part of the embolization function.

Figure 10:
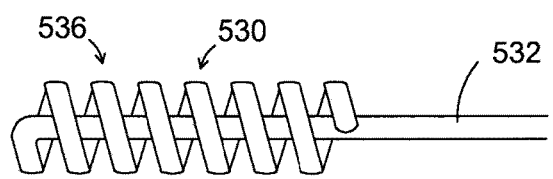
FIG. 10 is a side view of an alternative releasing element.

Various modifications can be made to the above described arrangement. For example, FIG. 10 shows an alternative releasing element 530 comprising a wire coil 536 with a release wire 532 attached to the distal end thereof and passing back through the coils itself to the proximal end thereof. In this case, at the stage shown in FIG. 8, withdrawal of the wire coil 536 begins from its distal end attached to the medical device 10, rather than from its proximal end.

Instead of assembling members 10, 16 and 30 by a rotational screwing procedure, the flexibility of the coil material may permit a more rapid method of assembly in which the coil 36 is inserted axially into the end of the helical wires 12, 18 and then sprung radially outwardly.

If desired, the release wire 32 can pass outside of deployment device 16, in which case device 16 can be a solid rod instead of a tube. In this modification, the initial movement of the wire at the end of the coil 36 is radially outwardly rather than radially inwardly. Also, an additional sheath or catheter may need to be provided around device 16 so as to provide a lumen in which the wire 32 can be withdrawn.

As described the devices 10 and 16 are generally cylindrical with a uniform circular cross-section. However, the or each device may be wholly or partly of a tapering configuration, either towards or away from the wire coil 36. In this case the wires 12 and/or 18 have a corresponding spiral or partly spiral configuration.

The cross-section of the wires 12, 18 and 36 is preferably circular, but may be elliptical, square or any other desired shape.

Figure 11:
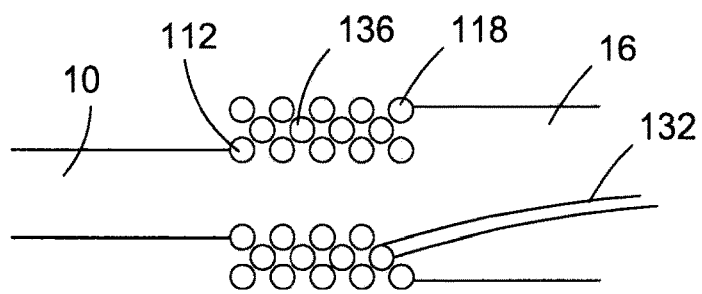
FIGS. 11 to 13 are partly sectional side views of the release members of delivery systems in accordance with further embodiments of the present invention.

FIG. 11 shows the release member of a delivery system in accordance with another embodiment of the present invention. Here, instead of being in substantial end-to-end axial alignment, the helically wound wires 112, 118 are arranged concentrically. Thus, helix formed by wire 112 attached to medical device 10 has a smaller diameter than the helix formed by wire 118 attached to the deployment device 16. Arranged radially between wires 112 and 118 is a wire coil 136 of intermediate diameter. The turns of coil 136 engage between the turns of wires 112, 118 to retain the devices 10 and 16 against mutual axial displacement. To remove the coil 136 and to release the arrangement, a pull is effected on a release wire 132 attached to, or integral with, the proximal end of the wire coil 136.

Figure 12:
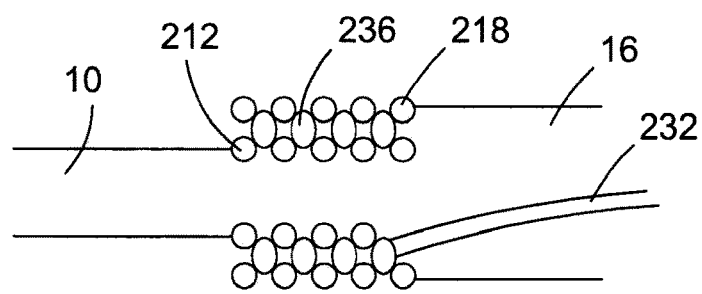

Whereas the wire forming the coil 130 of FIG. 11 has a circular cross-section, the wire forming the coil 236 of the embodiment shown in FIG. 12, has an elliptical cross-section. This is configured to provide a more secure engagement with the helical wires 212, 218. The cross-section of release wire 232 can be circular or also elliptical.

Figure 13:
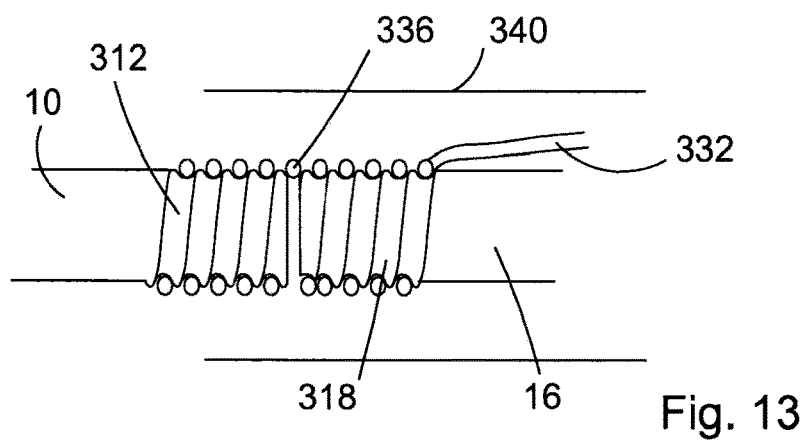

In a further embodiment, shown in FIG. 13, the helical wires 12, 18 are replaced by external helical threads on the outside of solid cylindrical members 312, 318. The members 312, 318 and their connected devices 10, 16 are held together axially by a wire coil 336. The wire of coil 336 has a diameter suitable for engaging with the threads of members 312, 318 and the pitch of the wire coil 330 has the same pitch as the threads. Withdrawal of the coil 336 to effect release begins by pulling on a release wire 332 within a surrounding sheath 340. The helical threads can have double-start thread forms, in which case the wire of coil 336 engages with alternate threads.

In a modification of the embodiment of FIG. 13, threads are provided on the interior of tubular members attached to devices 10 and 16 with the turns of wire coil 336 engaging with the internal threads.

Instead of a rigid sleeve 34, the assembly 80 may be provided in a relatively flexible protection sheath, which a user peels off the assembly before deployment.

The features of the various embodiments described above and their modifications may be substituted for or combined with one another as desired.

The invention claimed is:

1. A delivery system for a detachable medical device, the system comprising the detachable medical device having a first release portion, a deployment member having a second release portion, and a releasing element comprising a wire coil having a proximal end and a pull release wire attached to the proximal end, wherein the first and second release portions each having a helical element having windings defining a respective helical wound path therebetween, the wire coil of the releasing element and the windings of the first and second release portions having substantially the same diameter and pitch, such that the wire coil of the releasing element engages both of the helical wound paths between the windings of the first and second release portions to hold the first and second release portions together, the releasing element being detachable from the first and second release portions by a pull on the release wire, the pull allowing the proximal end of the wire coil to move slightly radially inwardly and then axially in the proximal direction, whereby to detach the first and second release portions from each other.

2. The system according to claim 1, wherein the first and second release portions are substantially in alignment and wherein each of the first and second release portions comprises a respective helically wound wire with a hollow core, the wire coil of the releasing element having turns which engage with end turns of the respective helically wound wire of both the first and second release portions.

3. The system according to claim 2 wherein ends of the respective helically wound wires of the first and second release portions are in a substantially mutually abutting relationship.

4. The system according to claim 2, wherein the second release portion comprises a tubular part at an end remote from the first release portion, and the release wire extends through the tubular part.

5. The system according to claim 2, wherein the wire coil of the releasing element is formed of a material that is substantially softer than a material of the respective helically wound wire of both the first and second release portions.

6. The system according to claim 1, wherein the first and second release portions are substantially in alignment and wherein each of the first and second release portions comprises external threads, the wire coil of the releasing element having turns which engage with the external threads of both the first and second release portions.

7. The system according to claim 6, wherein the first and second release portions have a uniform circular cross-section.

8. The system according to claim 1 wherein the wire coil is of resilient material.

9. The system according to claim 1, in which the release wire is integral with the wire coil.

10. The system according to claim 1 wherein a diameter of the windings of the helical element of the first release portion, a diameter of the windings of the helical element of the second release portion, and a diameter of the wire coil of the releasing element are substantially the same.

11. The system according to claim 1 wherein the wire coil of the releasing element fits between the respective windings of the first release portion and the second release portion to fill the helical wound path of the first release portion and the second release portion.

12. An introducer system for an implantable medical device comprising an introducer device, a pusher member connected to the introducer device, and a handle movable relative to both the introducer device and the pusher member, a deployment member located distally of said pusher member and a medical device located distally of said deployment member, the medical device having a first release portion, the deployment member having a second release portion, and a releasing element which is arranged to interconnect the first and second release portions, the first and second release portions each having a helical element having windings defining a respective helical wound path therebetween and the releasing element comprising a wire coil having a proximal end, the wire coil engaging both of the helical wound paths between the windings of the first and second release portions to hold the first and second release portions together, the wire coil of the releasing element and the windings of the first and second release portions having substantially the same diameter and pitch, the releasing element being connected to said handle via a release wire, the arrangement being such that, upon a proximal movement of the handle relative to the rest of the introducer device, the releasing element is detachable from the first and second release portions, the proximal movement allowing the proximal end of the wire coil to move slightly radially inwardly and then axially in the proximal direction, whereby to detach the first and second release portions from each other.

13. The system according to claim 12, wherein the pusher member has an interior lumen and the release wire passes from the wire coil to the handle through the interior lumen.

* * * * *